United States Patent
Thakre et al.

(10) Patent No.: US 7,337,678 B2
(45) Date of Patent: Mar. 4, 2008

(54) MEMS FLOW SENSOR

(75) Inventors: Parag Thakre, Karnataka (IN); Atanu Phukan, Karnataka (IN); Nikhil Chandra, Andhrapradesh (IN); Sriharsha Aradhya, Karnataka (IN)

(73) Assignee: General Electric Company, Niskayuna, NY (US)

( * ) Notice: Subject to any disclaimer, the term of this patent is extended or adjusted under 35 U.S.C. 154(b) by 159 days.

(21) Appl. No.: 11/297,861

(22) Filed: Dec. 9, 2005

(65) Prior Publication Data

US 2007/0131279 A1    Jun. 14, 2007

(51) Int. Cl.
*G01F 1/37* (2006.01)
(52) U.S. Cl. .................................. 73/861.52
(58) Field of Classification Search ............. 73/861.52, 73/861.53, 861.71, 861.73, 861.76; 138/43–46
See application file for complete search history.

(56) References Cited

U.S. PATENT DOCUMENTS

| | | | |
|---|---|---|---|
| 4,290,314 A * | 9/1981 | Geronime ................ 73/861.52 |
| 4,403,514 A * | 9/1983 | Osborn ..................... 73/861.52 |
| 4,932,269 A | 6/1990 | Cammarata, III et al. |
| 4,989,456 A | 2/1991 | Stupecky |
| 5,554,805 A * | 9/1996 | Bahrton ........................ 73/202 |
| 5,970,801 A * | 10/1999 | Ciobanu et al. .......... 73/861.52 |
| 6,729,196 B2 * | 5/2004 | Moler et al. .............. 73/863.22 |
| 6,786,036 B2 * | 9/2004 | Kight ........................... 60/204 |
| 6,848,320 B2 * | 2/2005 | Miyajima et al. ............. 73/763 |
| 2005/0092106 A1 | 5/2005 | Sheplak et al. |
| 2005/0109122 A1 | 5/2005 | Misholi et al. |

\* cited by examiner

*Primary Examiner*—Jewel Thompson
(74) *Attorney, Agent, or Firm*—Jean K. Testa; Curtis B. Brueske

(57) ABSTRACT

A micro-electro-mechanical, micro-fluidic flow sensor (14) includes a flow separating element (15) for separating a first portion (24) of a fluid flow (25) from a second portion (26) of the fluid flow. The flow sensor also includes a flow obstructing member (17) disposed in the first portion of the flow for at least partially obstructing the first portion of the flow. The flow obstructing member deflects in response to the first portion of the flow so that a degree of partial obstruction of the first portion of the flow by the flow obstructing member varies in response to the first portion of the fluid flow.

34 Claims, 4 Drawing Sheets

MEMS FLOW SENSOR

FIELD OF THE INVENTION

The present invention is generally related to fluid flow sensors, and, more particularly, to a micro-electro-mechanical (MEMS) based micro-fluidic flow sensor for a biomedical machine performing a flow measurement.

BACKGROUND OF THE INVENTION

Biomedical flow meters, such as flow meters for respirator, ventilators, anesthesia-machines, and/or incubators, etc., need to have sufficient dynamic range and high resolution at low flow for required performance, for instance, to accurately determine exhalation and inhalation airflow of a patient using the machine. Conventional differential pressure based flow meters may use an orifice, venturi, or pitot tube to establish a pressure differential in a fluid flow which may be sensed and interpreted as a measure of the fluid flow. Typically, such flow meters require maintenance to keep them clean of mucus and water vapor that may be exhaled by a patient. Also, such flow meters lack the low end resolution and dynamic range capabilities that are typically required for respiratory flow measurements needed in biomedical applications.

DETAILED DESCRIPTION OF THE INVENTION

The inventors have developed an innovative MEMS based micro-fluidic flow sensor that overcomes the disadvantages of conventional flow sensors such as described above. Advantageously, the innovative MEMS based micro-fluidic flow sensor has the ability to directly provide an electronic output which can be processed more easily as compared to a differential pressure output provided by conventional flow sensors. In addition, significant cost savings may be realized compared to conventional flow sensors.

Flow sensors having variable orifices (that is, orifices that change in size responsive to a fluid flow parameter) have been proposed to achieve a desired dynamic range and low pressure resolution needed for measuring respiratory flows. However, such flow sensors typically transect an entire bore of a respirator tube conducting an airflow to be measured and may be susceptible to contamination, for example, by exhaled mucus and/or water vapor. Water vapor may result in water condensation forming inside the sensor which may affect the sensor's performance by causing the output of to sensor to drift over time.

Figure 1:
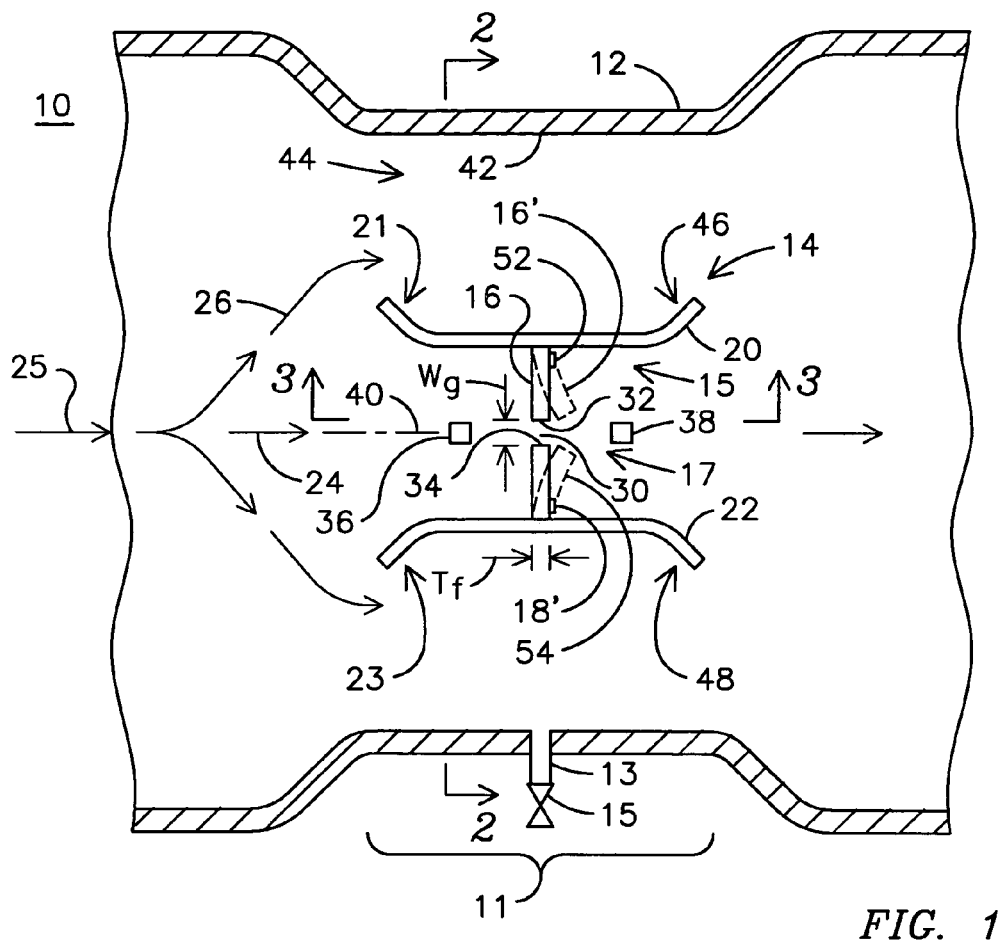
FIG. 1 is a diagram of an example flow meter comprising a MEMS flow sensor.

FIG. 1 is an exemplary diagram of a flow meter 10 comprising a MEMS flow sensor 14 that provides improved capability over conventional flow sensors such as are typically used in respiratory airflow measuring applications. The flow sensor 14 includes a flow separating element 15, such as two spaced apart walls 20, 22, for separating a first portion 24 of a fluid flow 25 flowing through a conduit 12 from a second portion 26 of the fluid flow 25. In an aspect of the invention, the fluid flow 25 may be an exhalation/inhalation airflow of a respirator patient. In another aspect, the fluid flow 25 may be a portion of an exhalation/inhalation airflow of a respirator patient, wherein the portion of the exhalation/inhalation airflow comprises the fluid flow 25 being conducted through the conduit 12.

The sensor 14 also includes a flow obstructing member 17 disposed in the first portion 24 of the flow 25 for at least partially obstructing the first portion 24 of the flow 25. The member 17 deflects in response to the first portion 24 of the flow 25 so that a degree of partial obstruction of the first portion 24 by the flow obstructing member 17 varies in response to the first portion 24. In an aspect of the invention, the flow obstructing member 17 may comprise one or more flaps 16, 18 extending from walls 20, 22 of the flow separating element 15. In an embodiment, the flow obstructing member 17 comprises a first flap 16 extending from a first wall 20 of the spaced apart walls 20, 22 towards a second flap 18 extending from a second wall 22 so that a gap 30 is defined between respective ends 32, 34 of the flaps 16, 18. While a two flap embodiment of a flow obstructing member 17 is described above, it should be understood that the number flaps used, and a geometry of those flaps, may be modified to achieve a desired flow measurement performance.

The gap 30 defined between the ends 32, 34 of the flaps 16, 18 allows the first portion 24 to flow therethrough. Because the flaps 16, 18 are deflectable in response to the first portion 24 of the flow 25, the gap 30 includes a variable geometry, such as a variable width, Wg, corresponding to a degree of deflection of the flaps 16, 18. For example, as a pressure of the flow 25 increases, and correspondingly, a pressure of the first potion 24, the flaps 16, 18 may be deflected away from the gap 30 as shown by the dotted lines indicating respective positions of the defected flaps 16', 18.' Consequently, a width of the gap 30 is increased, allowing more flow though the gap 30 compared to a less deflected position of the flaps 16, 18. It has been demonstrated by the inventors that improved airflow pressure measurements may be achieved over prior techniques by providing such a flow responsive, variable geometry gap 30.

In an aspect of the invention, a rigidity of the flaps 16, 18 may be controlled to achieve a desired deflection characteristic, and, correspondingly, a desired pressure response characteristic of the sensor 14. For example, a rigidity may be varied by controlling a thickness, Tf, of the flaps 16, 18, and/or a length L and height H of the flaps 16, 18. In an aspect of the invention, a thickness of the flaps 16, 18 may range from a few microns to tens of microns. For example, the thickness of the flaps 16, 18 may range from about 5 to about 20 microns.

Figure 3:
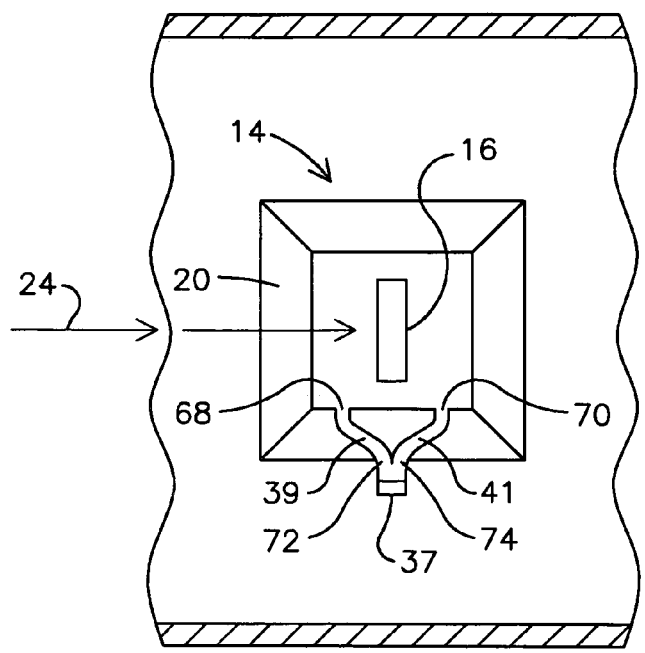
FIG. 3 is a cross sectional view of an example embodiment of the flow meter of FIG. 1 viewed along line 3-3.

In an embodiment, sensing of a flow parameter, such as a pressure of first portion 24 of the flow 25, may be accomplished using one or more pressure transducers 36, 38 disposed in communication with the first portion 24. For example, a first absolute pressure transducer 36 may be disposed upstream of the flow obstructing member 17 to sense a pressure of the first portion 24 upstream of the flaps. In an embodiment of the invention, the pressure transducers 36, 38 may include a piezo-resistive type absolute pressure sensor. A second transducer 38, as shown in FIG. 1, may be disposed downstream of the flow obstructing member 17 to sense a pressure of the first portion of the flow downstream of the flow obstructing member 17. The first transducer 36 and second transducer 38 may allow sensing respective absolute pressures across the flow obstructing member 17, which may be further processed electronically to generate a differential pressure. In an embodiment, one or more pressure transducers, such as the first transducer 36 and second transducer 38, may be longitudinally aligned with the gap 30 between the flaps 16, 18 as shown in FIG. 1. It should be understood that a configuration of the flaps may be modified to achieve a desired performance and or packaging configuration. In another embodiment depicted in FIG. 3, a single differential pressure sensor 37 may be used by routing an upstream 39 conduit having an inlet 68 upstream of the flap 16 and a downstream conduit 41 having an inlet 70 downstream of the flap 16 to the pressure sensor 37. For example, the pressure sensor 37 may be disposed at respective outlet ends 72, 74 of the conduits 39, 41 for measuring a pressure differential between the flow 24 at respective inlet ends 68, 70.

In another embodiment shown in FIG. 1, a stress transducer 52, 54, such as a piezo-resistive stress transducer, may be disposed on one or more of the flaps 16, 18 to detect a stress on the flap 16, 18 indicative of a fluid pressure forcing the flap 16, 18 to deflect. In an aspect of the invention, the piezo-resistive stress transducer 52, 54 may be integrally formed with the respective flap 16, 18.

In another aspect of the invention shown in FIG. 1, the flow meter 10 may include a conduit 12 comprising a flow acceleration zone 11 for conducting the fluid flow 25 therethrough. The flow sensor 14 may be disposed in the flow acceleration zone 11 so that the first portion 24 of the flow 25 flows through the sensor 14, and a second portion 26 of the flow 25 flows around the sensor 14. The flow acceleration zone 11 may include a venturi or orifice geometry, for example, to accelerate the flow 25 and limit a flow stalling effect that may be elevated by a flow impedance of the flow sensor 14. In another example embodiment, one or more walls 20, 22 of the flow separating element 15 may include a geometry effective to impart a higher velocity to the second portion 26 of the fluid flow 25 than a velocity imparted to the first portion 24 effective to conduct particulates in the fluid 25 within the second portion 26 instead of the first portion 24. By imparting a relatively higher velocity to the second portion 26, it is believed particulates, such as mucus, water droplets, or other particulate material that may interfere with proper functioning of the sensor 14 are carried away from the sensor 14 in the second portion 26. Furthermore, the higher velocity imparted to the flow advantageously increases a pressure drop across the flow sensor 14 thereby providing increased sensitivity of the flow measurement. In another aspect of the inventions, sharp edges of the flow meter structure are minimized to limit contamination by water condensation. In another embodiment of the invention, a drain 13 and valve 15 may be provided for selectively removing accumulated contaminants, such as water, from the conduit 12.

As shown in FIG. 1, the geometry of the flow separating element 15 may include walls 20, 22 having respective upstream end portions 21, 23 angled away from a centerline 40 of the acceleration zone 11. For example, the upstream end portions 21, 23 may be angled toward a conduit wall 42 of the conduit 12 for forming a narrowed region 44 between the upstream end portions 21, 23 and the conduit wall 42 effective to further accelerate the second portion 26 of the flow 25 flowing around the sensor 14. A geometry of the flow separating element 15 may also include walls 20, 22 having respective downstream end portis 46, 48 being angled away from a centerline 40 of the acceleration zone 11. For example, the downstream end portions 46, 48 may be angled away from about 30 to about 60 degrees from the centerline, and more preferably about 40 to about 50 degrees from the centerline. The downstream end portions 46, 48 may similarly be angled away from the centerline 40 to allow the sensor 14 to operate bi-directionally to accelerate the second portion 26, for example, when the flow 25 is traveling in a direction opposite to the flow direction indicated in FIG. 1.

Figure 2:
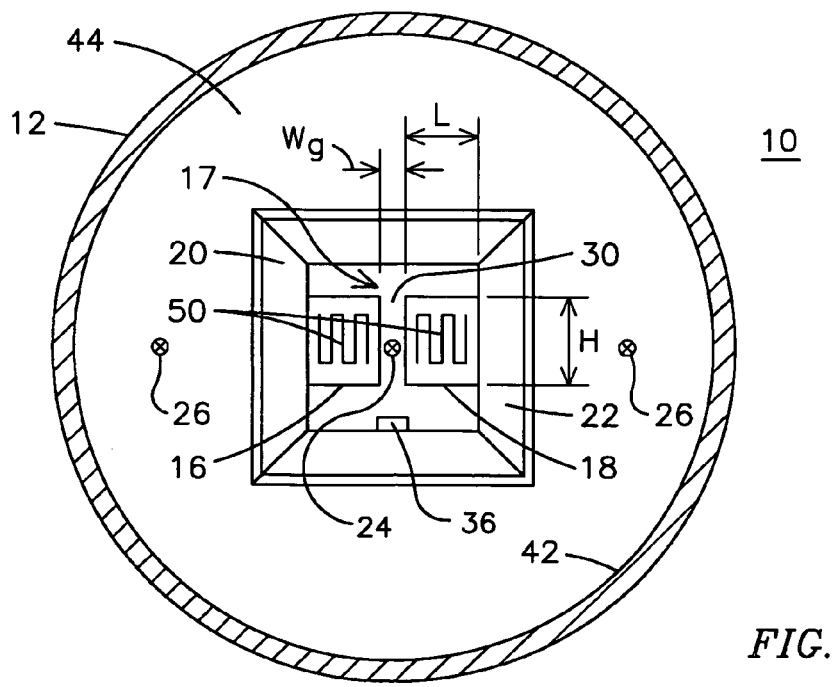
FIG. 2 is a cross sectional view of the example flow meter of FIG. 1 viewed along line 2-2.

FIG. 2 is a cross sectional view of the flow meter of FIG. 1 viewed along line 2-2. In an example embodiment of the invention, a distance, D, between the walls 20, 22 of the sensor 14 may range from about 900 to about 1100 microns. A length, L, of the flaps 16, 18 may range from about 400 to about 500 microns. A height, H, of the flaps 16, 18 may range from hundreds of microns to tens of microns. For example, a height, H, of the flaps 16, 18 may range from about 200 to about 400 microns. A width of the gap 30 between the flaps 16, 18, may range from hundreds of microns to tens of microns. For example, a width of the gap 30 between the flaps 16, 18, may range from about 10 microns to about 100 microns, and more preferably, from about 40 to about 60 microns.

While rectangular flaps 16, 18 defining a rectangular gap 30 and extending from respective straight walls 20, 22 of the flow separating element 17 are depicted in FIG. 1, the invention is not limited to a certain geometric configuration, and a variety of other flap, gap, and/or wall geometries may be used. For example, the sizes of the flaps 16, 18 may be varied in width, length, or both, to provide a desired flow characteristic through the gap 30. In addition, a geometric shape of the flaps 16, 18 and walls 20, 22 may be varied, such as by using curved shapes to achieve a desired flow sensing capability of the sensor 14.

Figure 4:
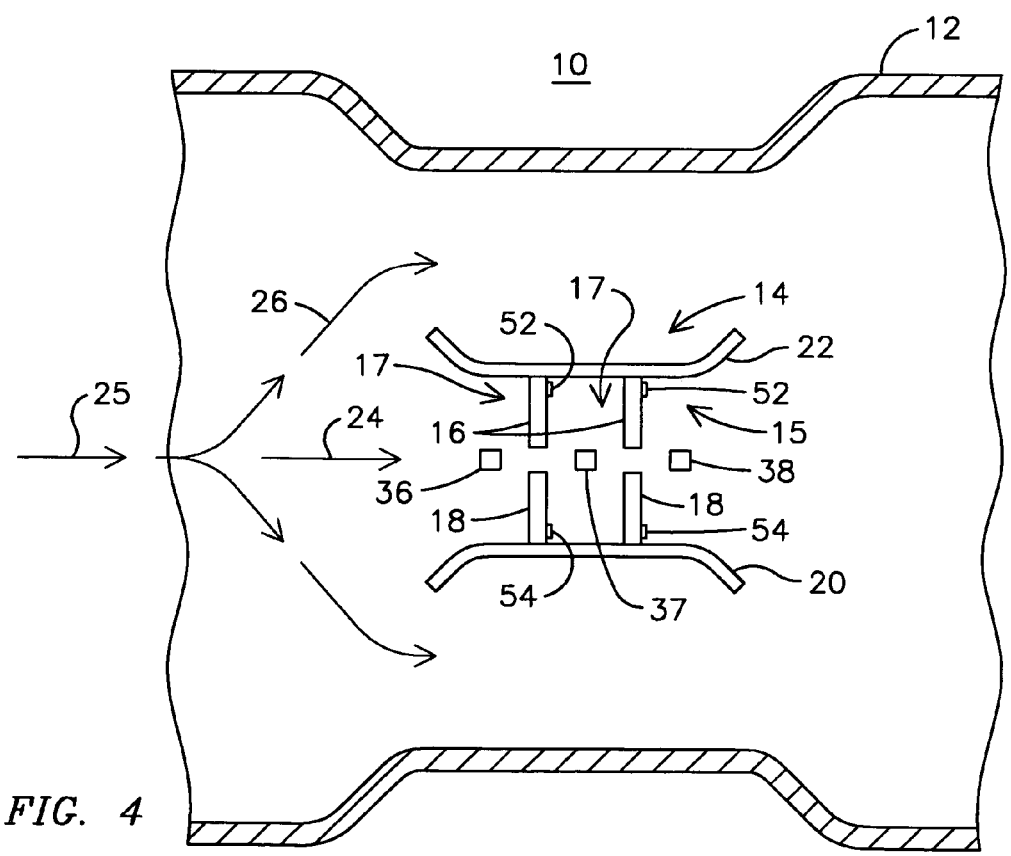
FIG. 4 is a diagram of an example embodiment of a MEMS-based flow meter.

In yet another embodiment shown in FIG. 4, two or more flow obstructing element 17, such as sets of flaps 16, 18, may be provided. Pressure sensors 36, 37, 38 may be provided at the upstream and downstream sides of each of the flow obstructing element 17, and/or pressure transducers 52, 54 may be disposed on the flaps 16, 18.

Figure 5:
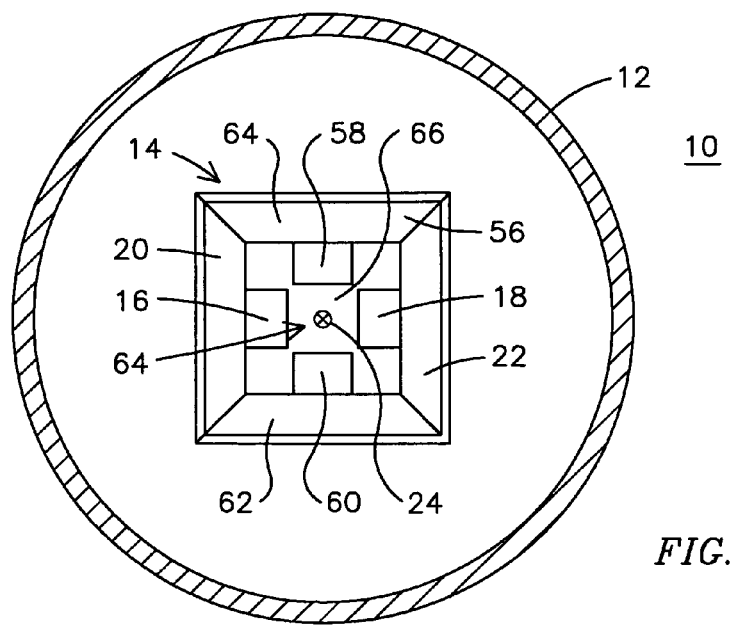
FIG. 5 is a cross sectional view of an example embodiment of a MEMS-based flow meter taken perpendicular to a direction of flow.

In an embodiment depicted in FIG. 5, the sensor 14 may take the form of a tubular member, such as a tube 56 having a rectangular cross section for directing the flow 25 to flow therethrough. The box may be disposed in the conduit 12 and include four walls 20, 22, 62, 64 with respective flaps 16, 18, 58, 60 extending from the four walls 20, 22, 62, 64 so that a gap 66 is formed between the flaps 16, 18, 58, 60 in a central region 64 of the tube 56.

Returning to FIG. 2, the sensor 14 may comprise a heating element 50 on-board the sensor 14 for limiting moisture condensation. For example, each flap 16, 18 may include a resistive type heating element 50 for heating the flap 16, 18 to limit moisture condensation on the flap 16, 18. A heating element 50 may be disposed anywhere on-board the sensor 14 to achieve desired heating of a portion of the sensor 14 proximate the heating element 50.

While exemplary embodiments of the sensor 14 have been described above in terms of a one way flow, the configuration allows bidirectional flow through the sensor 14 while still retaining the ability to measure flows therethrough. For example, in a respiratory flow meter embodiment, the flow sensor 14 may sense both inhalation (air moving in a first direction) and exhalation (air moving in an opposite direction) airflow.

Figure 6:
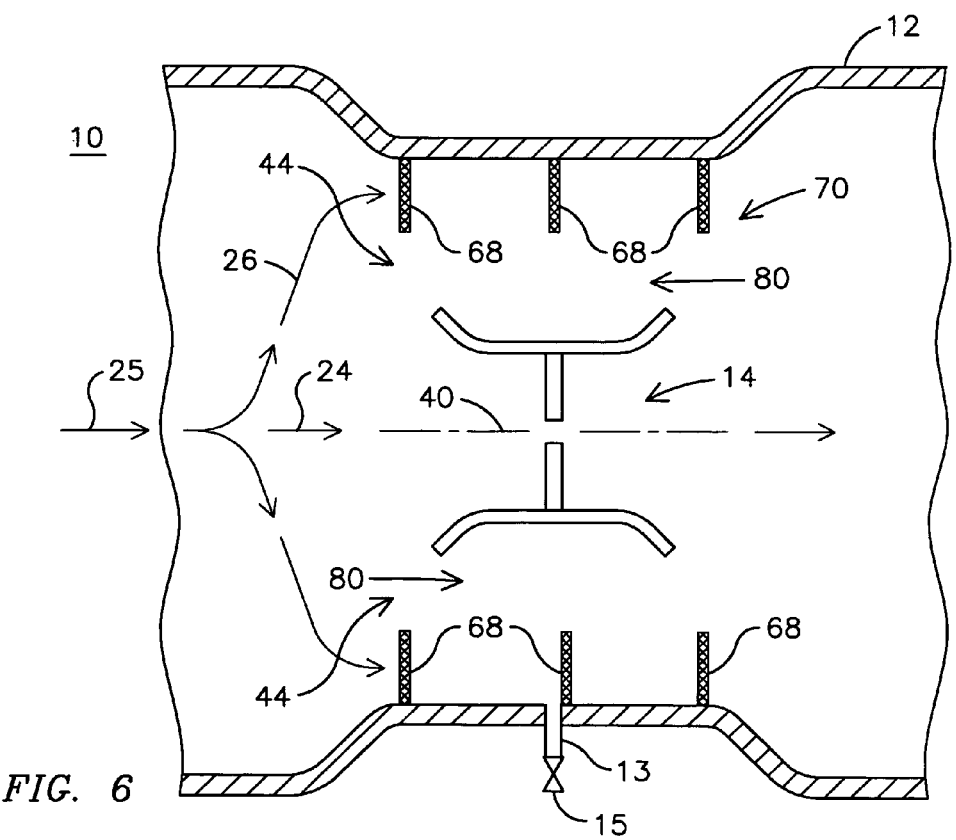
FIG. 6 is a diagram of an example flow meter comprising a MEMS flow sensor having an example contaminant entrapment structure.

FIG. 6 is a diagram of an example flow meter 10 comprising a MEMS flow sensor 14 and also including an example contaminant entrapment structure 70 for limiting contaminants, such as by water vapor and mucus that may adversely affect the function of the sensor 14. As shown in FIG. 6, the entrapment structure 70 may include one or more spaced apart annular sieves, or mesh rings 68, lining the conduit 12 near the sensor 14, such as in the narrowed region 44 around the sensor 14. The rings 68 may extend radially inward from the conduit 12 towards the centerline 40 so that an annular space 80 remains between the rings 68 and the sensor 14. The mesh rings 68 cause contaminates, such as water vapor, in the flow 26 to condense on the rings 68. A drain 13 and valve 15 may be provided for selectively removing accumulated condensed water from the conduit 12.

Figure 7:
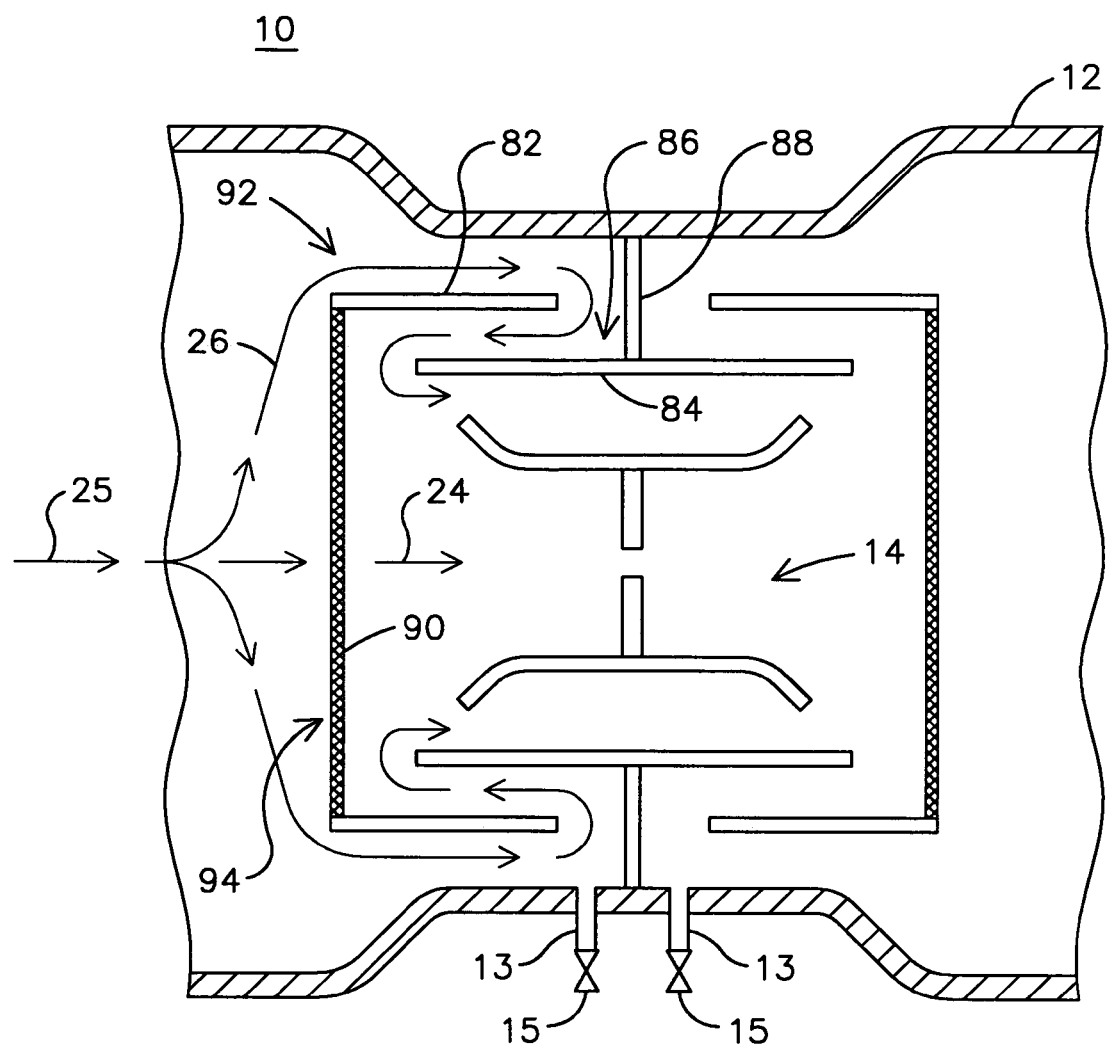
FIG. 7 is a diagram of an example flow meter comprising a MEMS flow sensor having another example contaminant entrapment structure.

FIG. 7 is a diagram of an example flow meter 10 comprising a MEMS flow sensor 14 having another example contaminant entrapment structure 92. The contaminant entrapment structure 92 may include radially spaced apart, axially oriented walls 82, 84 defining a circuitous path 86 for conducting at least a portion of the flow 25, such as flow 26, around the sensor 14. A flow blocking wall 88 may cause the flow 26 to make a 180 degree turn between walls 82, 84. The circuitous path 86 enhances condensation of water vapor in the flow 26, and the resulting condensed water may be collected and selectively drained via drains 13 and respective valves 15. A sieve, or mesh disk 90 may be positioned partially across an inlet 94 of the containment structure 92 for further forcing condensation and limiting mucus entry into the sensor 14. In an embodiment of the invention, the mesh disk 90 may extend to the radially outermost wall 82.

While various embodiments of the present invention have been shown and described herein, such embodiments are provided by way of example only. Numerous variations, changes and substitutions will occur to those of skill in the art without departing from the invention herein. Accordingly, it is intended that the invention be limited only by the spirit and scope of the appended claims.

What is claimed is:

1. A micro-electro-mechanical, micro-fluidic flow sensor comprising:
   a flow separating element for separating a first portion of a fluid flow from a second portion of the fluid flow, wherein the flow separating element includes a plurality of spaced apart walls; and
   a flow obstructing member disposed in the first portion of the flow for at least partially obstructing the first portion of the flow, the member deflecting in response to the first portion of the flow so that a degree of partial obstruction of the first portion of the flow by the flow obstructing member varies in response to the first portion of the fluid flow, wherein the flow obstructing member includes a first flap extending from a first wall of the spaced apart walls towards a second flap extending from a second wall of the spaced apart walls so that a gap is defined between the flaps having a variable geometry corresponding to a degree of deflection of the flaps, the flaps being compliant to the first portion of the fluid flow and being deflected in response to a flow parameter of the first portion of the fluid flow so that a degree of partial obstruction of the first portion of the fluid flow varies in response to the flow parameter.

2. The sensor of claim 1, further comprising a pressure transducer onboard the sensor responsive to a pressure of the fluid flow flowing through the sensor.

3. The sensor of claim 1, wherein the flow separating member comprises a tubular member.

4. The sensor of claim 3, wherein the flow obstructing member comprises a plurality of flaps extending from walls of the tubular member towards a central region of the tubular member so that a gap is defined between the flaps.

5. The sensor of claim 1, further comprising a pressure transducer onboard the sensor responsive to a pressure of the fluid flow flowing through the sensor.

6. The sensor of claim 1, wherein the sensor is integrally formed on a silicon substrate.

7. A micro-electro-mechanical flow meter comprising:
   a conduit comprising a flow acceleration zone for conducting a fluid therethrough;
   a micro-fluidic flow sensor disposed in the flow acceleration zone so that a first portion of the fluid flows through the sensor and a second portion of the fluid flows around the sensor, the sensor comprising:
   two spaced apart walls for directing the first portion of the fluid flow therebetween;
   first and second flaps extending from respective walls for partially obstructing the first portion of the fluid flow, the flaps being compliant to the first portion of the fluid flow and being deflected in response to a flow parameter of the first portion of the fluid flow so that a degree of partial obstruction of the first portion of the fluid flow varies in response to the flow parameter; and
   a first pressure transducer onboard the sensor responsive to a pressure of the first portion of the fluid flow flowing through the sensor.

8. The flow meter of claim 7, further comprising a gap defined between respective ends of the first and second flaps for allowing the fluid flow to flow unobstructed therethrough, the gap having a variable geometry responsive to the flaps being deflected away from each other in response to the flow parameter of the fluid flow.

9. The flow meter of claim 7, wherein a width of the gap ranges from about 10 microns to about 100 microns.

10. The flow meter of claim 7, wherein a width of the gap ranges from about 40 microns to about 60 microns.

11. The flow meter of claim 7, wherein the flow acceleration zone comprises geometry selected from the group consisting of a venturi and an orifice.

12. The flow meter of claim 7, wherein the walls comprise a geometry effective to impart a higher velocity to the second portion of the fluid flow than the first portion so that a pressure drop across the flow sensor is increased to provide a corresponding increased sensitivity for flow measurement.

13. The flow meter of claim 7, wherein the walls comprise respective upstream end portions being angled away from a centerline of the acceleration zone.

14. The flow meter of claim 13, wherein an angle of the end portions away from the centerline ranges from about 30 to about 60 degrees.

15. The flow meter of claim 13, wherein an angle of the end portions away from the centerline ranges from about 40 to about 50 degrees.

16. The flow meter of claim 13, wherein the walls comprise respective downstream end portions being angled away from a centerline of the acceleration zone.

17. The flow meter of claim 7, wherein the first pressure transducer is disposed upstream of the flaps.

18. The flow meter of claim 7, further comprising a second pressure transducer disposed downstream of the flaps.

19. The flow meter of claim 7, further comprising a first conduit having an inlet disposed upstream of the flaps and a second conduit having an inlet disposed downstream of the flaps, the disposed at respective outlet ends of the conduits for measuring a pressure differential between the flow at respective inlet ends.

20. The flow meter of claim 7, wherein the walls comprise respective upstream end portions being angled away from a centerline of the acceleration zone.

21. The flow meter of claim 7, further comprising a heating element on-board the sensor for limiting moisture condensation.

22. The flow meter of claim 7, wherein the pressure sensor comprises a piezo-resistive type pressure sensor.

23. The flow meter of claim 7, wherein a thickness of the flaps ranges from about 5 to about 20 microns.

24. The flow meter of claim 7, wherein a length of the flaps ranges from about 400 to about 500 microns.

25. The flow meter of claim 7, wherein a height of the flaps ranges from about 200 to about 400 microns.

26. The flow meter of claim 7, wherein a distance between the walls ranges from about 900 to about 1100 microns.

27. The flow meter of claim 7, wherein the sensor is integrally formed on a silicon substrate.

28. The flow meter of claim 7, further comprising a second set of flaps disposed downstream of the first and second flaps.

29. The flow meter of claim 7, further comprising a drain disposed in the conduit to allow fluids accumulated in the conduit to be drained away from the conduit.

30. The flow meter of claim 29, further comprising a valve to selectively open and close the drain.

31. The flow meter of claim 7, further comprising a contaminant entrapment structure disposed within the conduit proximate the flow sensor for limiting contaminants in the fluid from affecting an operation of the flow sensor.

32. The flow meter of claim 31, wherein the contaminant entrapment structure comprises a mesh ring annularly lining the conduit and extending radially inward from the conduit towards a centerline of the conduit so that an annular space remains between the ring and the sensor.

33. The flow meter of claim 31, wherein the contaminant entrapment structure comprises a circuitous path for conducting at least a portion of the fluid around the sensor.

34. The flow meter of claim 31, wherein the contaminant entrapment structure comprises a mesh disk at least partially across an inlet of the contaminant entrapment structure.

* * * * *